(12) United States Patent
Ota

(10) Patent No.: US 7,077,804 B2
(45) Date of Patent: Jul. 18, 2006

(54) LIGHT SOURCE APPARATUS FOR ENDOSCOPE

(75) Inventor: Noriko Ota, Saitama (JP)

(73) Assignee: PENTAX Corporation, Tokyo (JP)

(*) Notice: Subject to any disclaimer, the term of this patent is extended or adjusted under 35 U.S.C. 154(b) by 176 days.

(21) Appl. No.: 10/777,064

(22) Filed: Feb. 13, 2004

(65) Prior Publication Data

US 2004/0210112 A1   Oct. 21, 2004

(30) Foreign Application Priority Data

Feb. 17, 2003   (JP) ............................. 2003-038346

(51) Int. Cl.
*A61B 1/06* (2006.01)
*H01L 33/00* (2006.01)

(52) U.S. Cl. ...................... 600/180; 600/178; 600/181; 362/555; 362/574; 348/68

(58) Field of Classification Search ................ 600/178, 600/180, 181; 362/20, 250, 551, 554, 555, 362/574; 348/68
See application file for complete search history.

(56) References Cited

U.S. PATENT DOCUMENTS

| | | | |
|---|---|---|---|
| 4,924,856 A * | 5/1990 | Noguchi | 600/180 |
| 5,980,053 A * | 11/1999 | Hauser et al. | 362/20 |
| 6,318,887 B1 * | 11/2001 | Matsumoto | 362/574 |
| 6,602,186 B1 | 8/2003 | Sugimoto et al. | |
| 6,733,441 B1 * | 5/2004 | Niida et al. | 600/178 |
| 6,929,605 B1 * | 8/2005 | Kurosawa | 600/178 |

FOREIGN PATENT DOCUMENTS

| | | |
|---|---|---|
| JP | 2866658 | 2/1998 |
| JP | 10108826 | 4/1998 |
| JP | 11305148 | 11/1999 |
| JP | 2000-210245 | 8/2000 |
| JP | 2002-72106 | 3/2002 |

OTHER PUBLICATIONS

English Language Abstract of JP 11-305148.

* cited by examiner

*Primary Examiner*—John P. Leubecker
(74) *Attorney, Agent, or Firm*—Greenblum & Bernstein, P.L.C.

(57) ABSTRACT

A light source apparatus for an endoscope including a main light source; a light guide member whose incident end face is opposed to the main light source and which guides light incident thereon to an emission end face thereof; an auxiliary light source which is activated to emit light when no light is emitted from the main light source and which is supported to move between a stand-by position in which the auxiliary light source is located out of a main light path between the main light source and the incident end face and an operative position in which the auxiliary light source is located in the main light path and is opposed to the incident end face when the main light source is inoperative; and an auxiliary light source emission control device for driving the auxiliary light source at a continuous emission mode to emit light of a predetermined intensity or at an intermittent emission mode to emit light of an intensity higher than the predetermined intensity.

10 Claims, 8 Drawing Sheets

Fgi. 5

LIGHT SOURCE APPARATUS FOR ENDOSCOPE

BACKGROUND OF THE INVENTION

1. Field of the Invention

The present invention relates to a light source apparatus for an electronic scope or a fiber scope.

2. Description of the Related Art

A high intensity lamp, such as a halogen lamp, a mercury vapor lamp or a metal halide lamp is used as a light source of a light source apparatus for an endoscope. If the light source goes off due to expiration of the service life thereof or trouble during examination or an operation using an endoscope, it is necessary to replace the light source or the light source apparatus with a new one. It is not desirable that the endoscope stays in a body cavity of a patient during the replacement.

To solve this problem, it has been proposed to provide a separate auxiliary light source in addition to a main light source of a high intensity lamp, wherein if the main light source goes off, the auxiliary light source is used to illuminate a body cavity of a patient, so that an insertion portion of an endoscope can be entirely removed from the body cavity under the illumination by the auxiliary light source. For example, see Japanese Patent Applications Laid-open Nos. 2000-210245, H10-108826, and 2002-72106.

As the auxiliary light source is provided for emergency use and is seldom used, it is preferable that the auxiliary light source be as small as possible and tend not to deteriorate due to aging. However, if the auxiliary light source is made of a high intensity LED, the amount of light emitted therefrom is smaller than that of the main light source and, hence, there is a possibility that the amount of light of the auxiliary light source which may be sufficient for a fiber scope is insufficient for use with an electronic scope and, consequently, an image captured by a picked-up image of the electronic scope is too dark.

It is an object of the present invention to eliminate the drawbacks of the prior art mentioned above by providing a light source apparatus for an endoscope in which an on/off state of an auxiliary light source can be controlled.

SUMMARY OF THE INVENTION

The present invention eliminates the drawbacks of the prior art mentioned above by providing a light source apparatus for an endoscope in which an on/off state of an auxiliary light source can be controlled.

According to an aspect of the present invention, a light source apparatus for an endoscope including a main light source; a light guide member whose incident end face is opposed to the main light source and which guides light incident thereon to an emission end face thereof; an auxiliary light source which is activated to emit light when no light is emitted from the main light source and which is supported to move between a stand-by position in which the auxiliary light source is located out of a main light path between the main light source and the incident end face and an operative position in which the auxiliary light source is located in the main light path and is opposed to the incident end face when the main light source is inoperative; and an auxiliary light source emission control device for driving the auxiliary light source at a continuous emission mode to emit light of a predetermined intensity or at an intermittent emission mode to emit light of an intensity higher than the predetermined intensity.

It is desirable for the light source apparatus to be used with an endoscope processor to which an electronic endoscope or a fiber scope can be mounted, and wherein said auxiliary light source emission control device drives the auxiliary light source to emit light intermittently in synchronization with an image pickup operation of an image pickup device of the electronic endoscope when the electronic endoscope is connected to the endoscope processor and drives the auxiliary light source to emit light continuously when the fiber scope is connected to the endoscope processor.

It is desirable for the auxiliary light source emission control device to drive the auxiliary light source to emit light intermittently in synchronization with a vertical synchronizing signal to drive the image pickup device.

It is desirable for the auxiliary light source to include an LED. The auxiliary light source emission control device drives the LED at a constant current smaller than an absolute maximum rated value of a forward current of the LED when the continuous emission is carried out, and drives the LED at a pulse current of which a crest value is higher than the absolute maximum rated value of the forward current when the intermittent emission is carried out.

It is desirable for the light source apparatus to include a selection switch device for selecting the intermittent emission of the auxiliary light source at a pulse current or the continuous emission thereof through the auxiliary light source emission control device.

It is desirable for the light source apparatus to include a sensor device for detecting whether the light guide member is mounted or the electronic endoscope is mounted, wherein said auxiliary light source emission control device drives the auxiliary light source at a pulse current when it is detected by the sensor device that an electronic endoscope having the light guide member is mounted.

The present disclosure relates to subject matter contained in Japanese Patent Application No.2003-38346 (filed on Feb. 17, 2003) which is expressly incorporated herein by reference in its entirety.

DESCRIPTION OF THE PREFERRED EMBODIMENT

Figure 1:
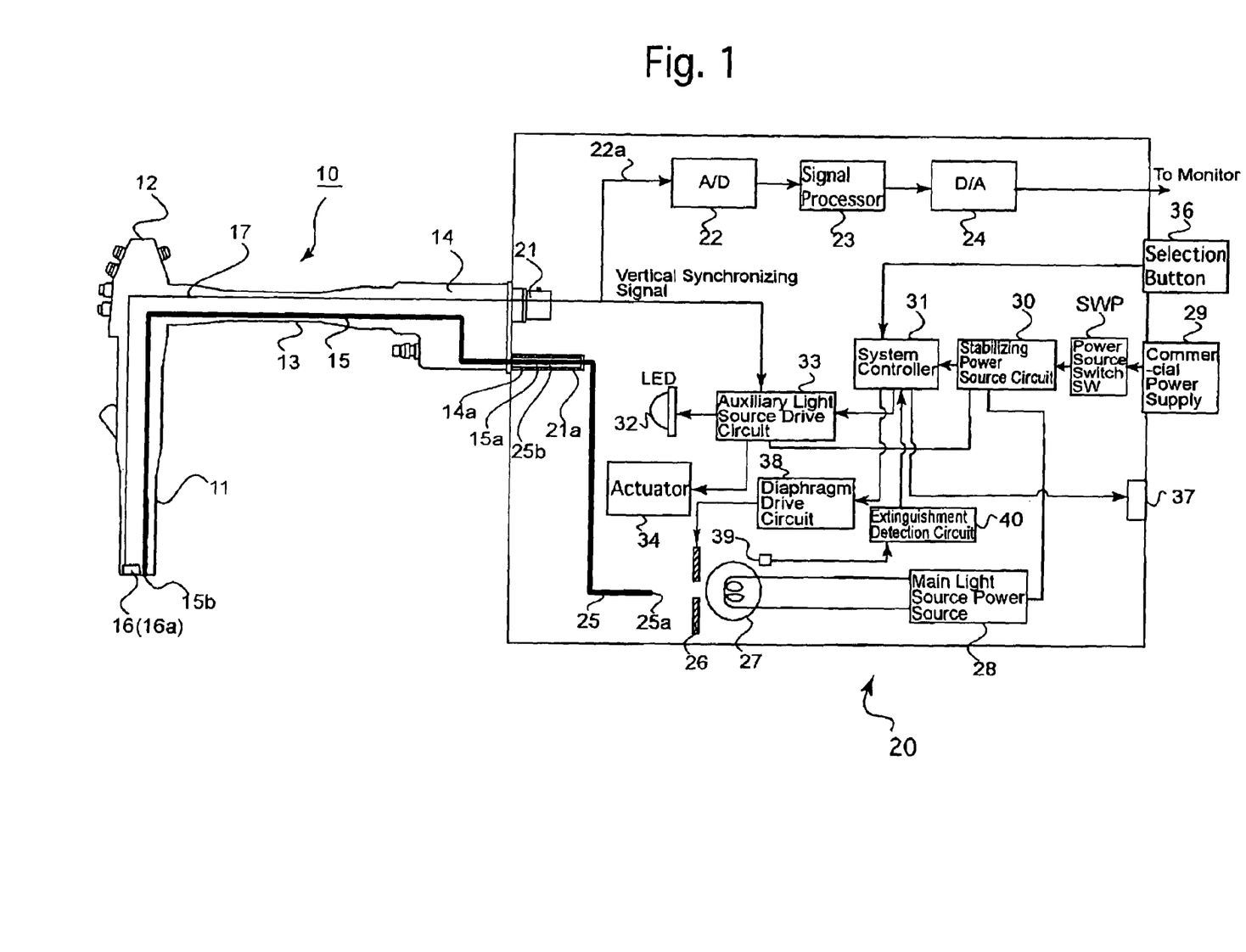
FIG. 1 is a block diagram of main components of a light source apparatus for an endoscope according to a first embodiment of the present invention.

FIG. 1 shows main components of a first embodiment of a light source apparatus applied to an electronic endoscope system, according to the present invention.

The electronic endoscope 10 is comprised of a flexible insertion portion 11, an operating portion 12 provided at an external end of the insertion portion 11, and a universal tube 13 connected to the operating portion 12. The insertion portion 11 is provided on its front end with a built-in electronic camera 16 including an image pickup lens and an image pickup device (CCD), etc. The electronic camera 16 can pickup an external object through a view window (object window) formed at the front end face of the insertion portion 11. The insertion portion 11 is provided on its front end face with an emission end face 15b of a light guide (a bundle of optical fibers) 15 as an illumination light guiding means and an outlet port of forceps channel (not shown), etc. The operating portion 12 is provided with operation buttons for controlling a motion image or still image capturing operation, etc., and a bending motion operating knob which operates the bending mechanism provided in the vicinity of the front end of the insertion portion 11, etc. The universal tube 13 is connected at its one end to the operating portion 12 and is provided at the other end with a connector assembly 14 having an electric connector and an optical connector 14a.

A processor 20 includes an A/D converter 22, a signal processing circuit 23, and a D/A converter 24, as an image signal processing system which processes an image signal picked up by the electronic camera 16. A signal cable 17 extends in the insertion portion 11, the operating portion 12 and the universal tube 13, and is connected at its one end to the electronic camera 16 and at the other end to a pin of the electric connector of the connector assembly 14. An image cable 22a is connected at its one end to a pin of an electric connector provided in the processor 20 and at the other end to an input port of the A/D converter 22. The electronic camera 16 and the A/D converter 24 are connected to each other through the signal cable 17, the electric connector of the connector assembly 14, an electric connector of the connector portion 21, and the image cable 22a. A TV monitor which displays an image picked up by the electronic camera 16 through a video encoder (not shown) is connected to the D/A converter 24. An operator operates the electronic endoscope 10 while viewing an image through the TV monitor. An external memory device, such as a video deck, which stores the image and an image signal input terminal of a personal computer, etc., in addition to the TV monitor can be connected to the D/A converter 24.

The light guide 15 extends from the front end of the insertion portion 11 and in the insertion portion 11, the operating portion 12 and the universal tube 13 and is connected at the other end to the optical connector 14a of the connector portion 14. The optical connector 14a is connected to the optical connector 21a of the connector portion 21 when the connector portion 14 is connected to the connector portion 21, so that the incident end face 15a of the light guide 15 is optically connected to the emission end face 25b of the light guide 25 (a bundle of optical fibers). The other end face of the light guide 25, i.e., the incident end face 25a is arranged so as to receive the illumination light emitted from the main light source 27. A diaphragm 26 is provided in a main light path between the main light source 27 and the incident end face 25a, so that the amount of light to be received by the incident end face 25a can be controlled by opening and closing the diaphragm 26. The diaphragm 26 is controlled by a system controller 31 through a diaphragm drive circuit 38.

The illumination light emitted from the main light source 27 and made incident upon the incident end face 25a is transmitted through the light guide 25, the emission end face 25b, the incident end face 15a, and the light guide 15, and is emitted externally from the illumination window at the front end of the insertion portion 11 through the emission end face 15b of the light guide 15 to illuminate a body cavity.

The emission of the main light source 27 is controlled by the main light source power source 28. The main light source power source 28 controls the activation of the main light source 27 by an electric current stabilized in a stabilizing power source circuit 30 which receives the electric power supplied from a commercial power supply 29.

The main light source 27 is usually made of a high intensity lamp, such as a halogen lamp, a mercury vapor lamp, or a metal halide lamp and is mounted to a lamp socket having a reflector shade. The light emitted from the main light source 27 is effectively converged onto the incident end face 25a of the light guide 25 by a condenser lens (not shown). The main light source 27 and the light guide 25 are arranged so that the convergence point of the light from the main light source 27 is identical to the incident end face 25a.

The processor 20 includes an auxiliary light source 32 which irradiates illumination light in place of the main light source 27 when the latter goes off due to expiration of the service life thereof or trouble. The auxiliary light source 32 is made of a high intensity LED 32a in the illustrated embodiment (FIG. 4(A)). The extinguishment of the main light source 27 is detected by an optical sensor 39 and an extinguishment detection circuit 40. The extinguishment detection signal is transmitted to the system controller 31. When the auxiliary light source drive circuit 33 receives a signal to turn the auxiliary light source 32 ON, supplied from the system controller 31, the activation of the auxiliary light source 32 is controlled by the auxiliary light source drive circuit 33. Note that the auxiliary light source drive circuit 33 operates at a constant-voltage current supplied from the stabilizing power source circuit 30.

The auxiliary light source drive circuit 33 moves the auxiliary light source 32 through an actuator 34 between a stand-by position in which the auxiliary light source 32 is located out of the main light path and an operative position (auxiliary light emission position) in which the auxiliary light source 32 is opposed to the incident end face 25a in the main light path and emits light. When the auxiliary light source 32 is turned ON, the system controller 31 flickers an auxiliary light source emission indication lamp 37 provided on the outer surface of the processor 20 to thereby indicate that the auxiliary light source 32 is turned ON.

The auxiliary light source 32 is normally held in the stand-by position out of the main light path and is inoperative.

Figure 2:
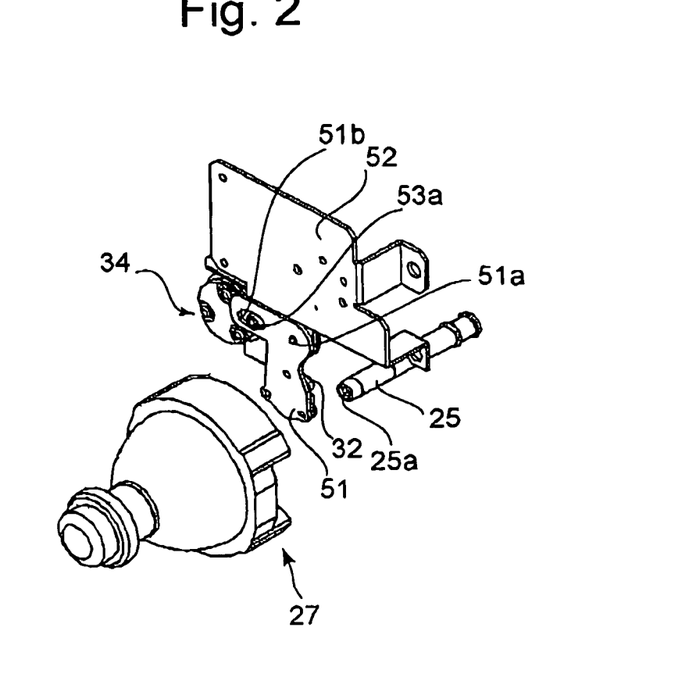
FIG. 2 is a perspective view of an auxiliary light source moving mechanism in a stand-by position of an auxiliary light source, according to a first embodiment of the present invention.
Figure 3:
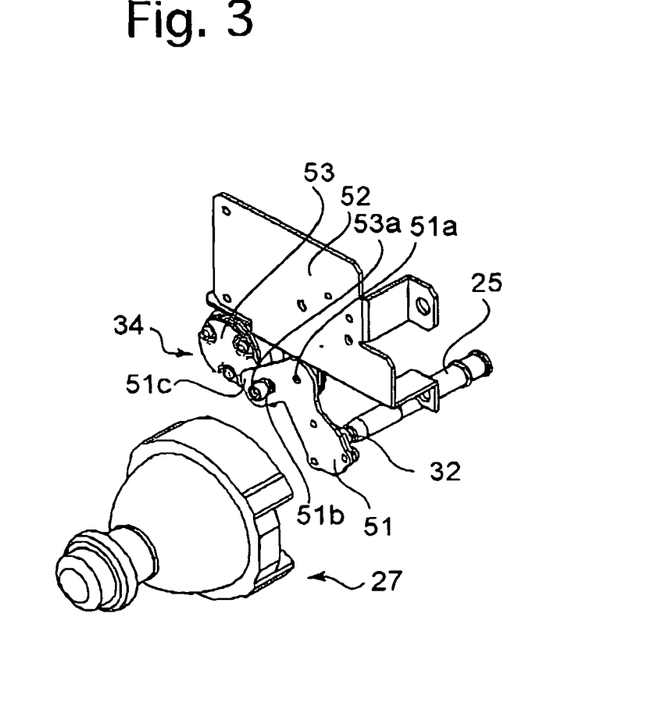
FIG. 3 is a perspective view of an auxiliary light source moving mechanism in an operative position of an auxiliary light source, according to a first embodiment of the present invention.

The mechanical structure of the light source apparatus will be discussed with reference to FIGS. 2 and 3. FIGS. 2 and 3 are perspective views of an auxiliary light source moving mechanism in the first embodiment of the present invention. In a stand-by position shown in FIG. 2, the main light source 27 normally emits light and in an auxiliary light emission position shown in FIG. 3, the auxiliary light source 32 is moved to the operative position and emits light.

The auxiliary light source 32 is secured to one end of an L-shaped lever 51. The L-shaped lever 51 is rotatably connected at its corner end to a retainer plate 52 through a shaft 51a and is connected at the other end to the actuator 34. The actuator 34 is a rotary actuator which is provided with a rotary plate 53 which is connected to a rotating shaft (not shown) that is paralleled to the main light path and which is provided with an eccentric shaft 53a which is fitted in an elongated hole 51b formed in one of the arms of the L-shaped lever 51 and extending along the arm.

When no electricity is supplied to the actuator 34 in accordance with the control signal from the auxiliary light source drive circuit 33, the rotary plate 53 is held in an initial position and the lever 51 is also held in an initial position. The initial position corresponds to the normal position in which the auxiliary light source 32 secured to one end of the L-shaped lever 51 is held in the stand-by position out of the main light path.

When the actuator 34 is supplied with electricity in accordance with the control signal supplied from the auxiliary light source drive circuit 33, the rotary plate 53 is rotated in the clockwise direction by a predetermined angle and the eccentric shaft 53a which is fitted in the elongated hole 51b is moved, so that the rotation of the L-shaped lever 51 about the shaft 51a in the counterclockwise direction takes place. As a result, the auxiliary light source 32 is moved to the operative position, i.e., the auxiliary light emission position in which the auxiliary light source faces the incident end face 25a. The auxiliary light source 32 is held in the operative position while the actuator 34 is supplied with electricity. When the auxiliary light source drive circuit 33 receives an auxiliary light emission signal from the system controller 31, the auxiliary light source drive circuit 33 supplies the auxiliary light source 32 with electricity to thereby turn the auxiliary light source ON and move the auxiliary light source 32 to the auxiliary light emission position.

Note that as the main light source 27 has a high temperature while it emits light, a cooling fan (not shown) is provided to cool the main light source 32. Also, if the auxiliary light source 32 cannot be cooled sufficiently by circulation of the cooling air produced by the cooling fan, an auxiliary light source cooling means can be provided in accordance with need.

The auxiliary light source drive circuit 33 drives the auxiliary light source 32 in two emission modes. Namely, in a first emission mode which is a steady-state current emission mode (continuous emission mode), the auxiliary light source 32 is activated at a constant current. In a second emission mode which is a pulse-current emission mode (intermittent emission mode), the auxiliary light source 32 is activated in synchronization with the accumulation of electric charges by the electronic camera 16 (exposure operation of the electronic camera 16). The emission modes are selected or switched in accordance with the position of a selection button (switch) 36 which is provided on the processor 20 and is operated manually by a user, through the system controller 31.

Figures 4A, 4B, 4C:
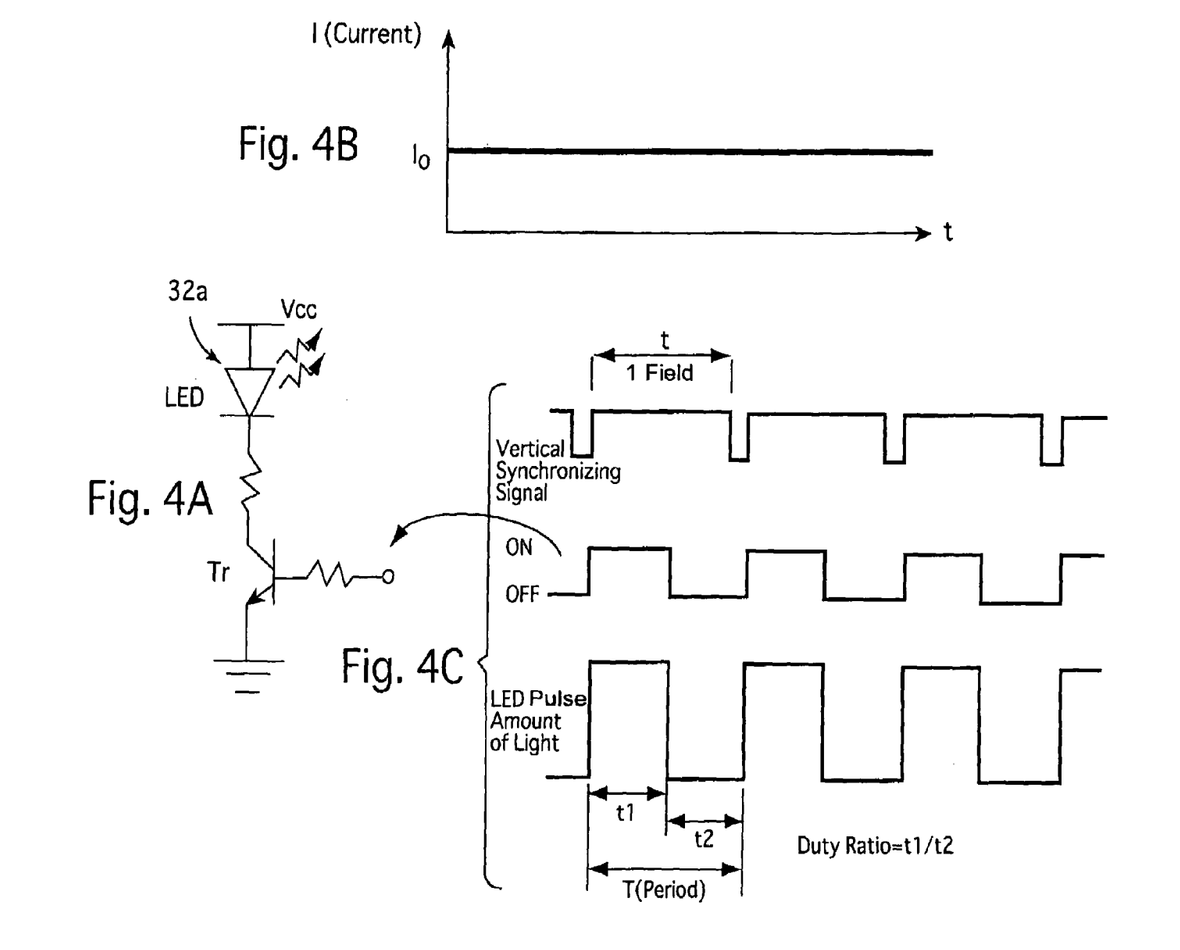
FIGS. 4A, 4B and 4C are timing charts of an auxiliary light source activating operation in a first embodiment of the present invention, by way of example.

The emission of light by the auxiliary light source 32 at the steady-state current emission mode and at the pulse-current emission mode will be explained with reference to the timing charts shown in FIGS. 4(B) and 4(C). FIG. 4(A) shows an example of an emission drive circuit of the auxiliary light source 32 (light emitting diode 32a). In the emission drive circuit, when a predetermined positive voltage is applied to the base of the transistor Tr, the transistor Tr is turned ON, that is, the emitter and the collector are connected, so that the current is supplied from Vcc (the voltage source) to the light emitting diode 32a. Consequently, the light emitting diode 32a emits light. When the base voltage of the transistor Tr becomes zero (ground level), the transistor Tr is turned OFF to interrupt the supply of the current (connection of the emitter and the collector is interrupted). As a result, the light emitting diode 32a is turned OFF. The emission drive circuit can control the current flowing through the transistor Tr by controlling the base voltage, the time in which the base voltage is applied, and the time interval of the application of the voltage. Namely, in this embodiment, the base voltage of the transistor Tr is controlled by the auxiliary light source drive circuit 33 to thereby activate the light emitting diode 32a at a constant-current or a pulse-current.

At the steady-state current emission mode, the auxiliary light source 32 continuously emits light at a constant current Io below the absolute maximum rated value of forward current of the auxiliary light source 32 (FIG. 4(B)). At the pulse-current emission mode, the intermittent emission of the auxiliary light source occurs in synchronization with the vertical synchronizing signal of the image signals output from the electronic camera 16. Namely, supply of the electricity begins in synchronization with the raising of the vertical synchronizing signal at which the exposure of the CCD begins (accumulation of the charges begins). At the completion of the exposure (before a subsequent vertical synchronizing signal is output), the electricity supply to the light emitting diode is stopped (light emission is stopped). Thus, the auxiliary light sourc is activated at a pulse-current under a so-called PWM control (FIG. 4(C)).

In the case that the electronic camera 16 is a video camera of a standard TV system (e.g., NTSC system), the photographing interval is 1/60 sec (about 17 ms) for photographing 60 fields or 1/30 sec (about 33 ms) for photographing 30 frames. The time for one exposure is shortened by a time in which the charge transfer time in synchronization with the vertical synchronizing signal is inserted. In this embodiment which is applied to the field photographing, it is assumed that the time for one field is t. The period T of the pulse emission of the auxiliary light source 32, which is identical to the field photographing interval is 1/60 sec (about 17 ms), which s slightly longer than the one filed time t. Note that if a CCD having a high speed electronic shutter function is used in place of a diaphragm, the one field time t is further shortened.

In this embodiment, the transistor Tr is turned ON by applying a voltage which is greater than the positive voltage applied to the base of the transistor (switching transistor) Tr at the steady-state current emission mode, by a predetermined value, in synchronization with (raising of) the vertical synchronizing signal by which the electronic camera 16 is driven. The drive current greater than the current Io is supplied to the light emitting diode 32a, so that the light emitting diode emits light with a higher intensity than that at the steady-state current emission mode. After the lapse of a predetermined time, when the voltage supply to the base of the transistor Tr is stopped to turn the transistor Tr OFF, the electricity supply to the light emitting diode 32a is interrupted and no light emission occurs. Assuming that the emission time and extinguishment time in one period of the pulse-based emission are t1 and t2, respectively, the duty ratio is represented by t1/T. Note that t1+t2=T.

Figure 5:
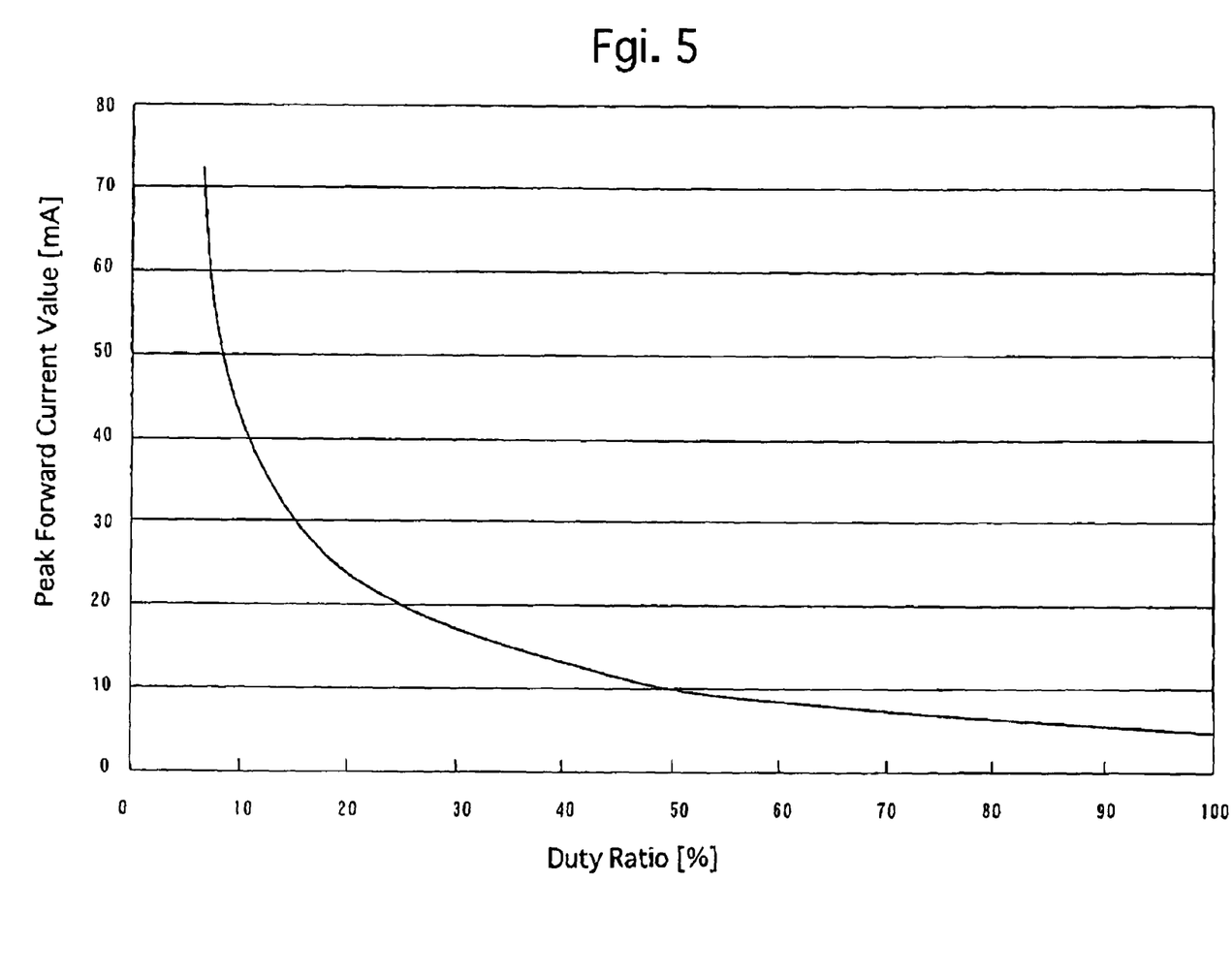
FIG. 5 is a graph showing the amount of light of an auxiliary light source when the auxiliary light source is activated with constant-current and when the auxiliary light source is activated with pulse-current at different duty ratios, in a first embodiment of the present invention.

In case of the pulse-current emission, it is only needed that the mean value of the drive current of the light emitting diode is below the absolute maximum rated value of the forward current. Therefore, the crest value (peak forward current value) of the drive current can be made higher than the absolute maximum rated value of the forward current as the duty ratio is reduced. FIG. 5 is a graph shows a relationship between the duty ratio and the peak forward current value (peak forward current—duty ratio characteristics) at the pulse-current emission mode.

The duty ratio is appropriately set in accordance with the necessary exposure time based on the field t, etc., and the pulse current of the light emitting diode LED is appropriately set in accordance with the set duty ratio and the peak forward current value—duty ratio characteristics. For example, if the duty ratio is 50%, the maximum rated value of the peak forward current is 10 mA, based on the peak forward current value—duty ratio characteristics shown in FIG. 5. The maximum rated value of the peak forward current thus obtained is approximately double the maximum rated value of the peak forward current (approximately 5 mA) when the duty ratio is 100% (i.e., at the steady-state current emission mode). Thus, it is possible to set the peak forward current value of the light emitting diode LED at the pulse-current emission mode larger than the maximum rated value of the peak forward current at the steady-state current emission mode (i.e., the absolute maximum rated value of the forward current). Namely, it is possible to make the intensity of the light emitting diode LED at the pulse-current emission mode higher than that at the steady-state current emission mode.

Next, the light emitting operation of the main light source and the auxiliary light source will be discussed with reference to an emission control flow chart shown in FIG. 6. The system controller 31 enters this emission control flow chart when the power source switch SWP is turned ON to supply the system controller with electricity from the commercial power supply 29. In the specification and the drawings, each operation step is represented by S. In this flow chart, whether or not the power switch SWP is operated is checked (S11). If the power switch SWP is not operated, the main light source 27 and the auxiliary light source 32 are turned OFF and the control ends (S11; N, END).

If the power switch SWP is operated, the main light source 27 is turned ON and the ON-state of the main light source is maintained, provided that the current of the main light source is not zero (S11; Y, S15, S17, N, S11). The operations mentioned above are repeated while the power switch SWP is ON and the main light source is supplied with electricity.

If the main light source 27 is out of order or the amount of the current of the main light source is reduced because of an operation of a safety device for some reasons (S17; Y), the main light source 27 is turned OFF (S19) and the actuator 34 is driven to move the auxiliary light source 32 to the operative position (S21). The auxiliary light source 32 is turned ON and the auxiliary light source emission indication lamp 37 is flickered to indicate that the light source is switched to the auxiliary light source (S23). The control does not proceed until the power switch SWP is turned OFF (S25). If the power switch SWP is turned OFF, the auxiliary light source 32 is turned OFF and the actuator 34 is driven to retract the auxiliary light source 32 to the stand-by position and the emission operation ends (S25; Y, S27, S29, END).

As may be understood from the foregoing, when the auxiliary light source 32 is turned ON, a user operates the operating portion 12 while viewing the TV monitor to remove the insertion portion 11 from the patient's body cavity and turns the power switch SWP OFF. Thus, the main light source 27 can be replaced.

Figure 7:
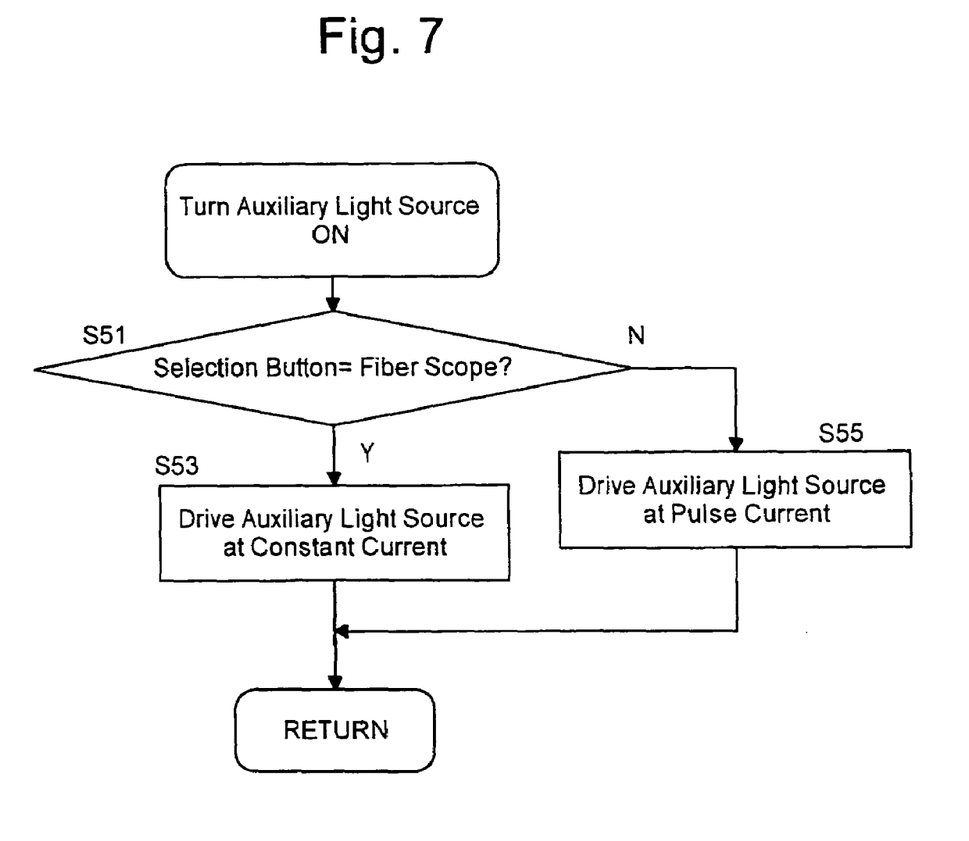
FIG. 7 is a flow chart of an operation to turn an auxiliary light source ON in a first embodiment of the present invention.

The operation to turn the auxiliary light source ON at S23 will be discussed with reference to FIG. 7. In this routine, whether or not the fiber scope is selected by the selection button (not shown) is checked (S51). If the fiber scope is selected, the auxiliary light source drive circuit 33 activates the auxiliary light source 32 at a constant current and the control is returned (S51; Y, S53, RETURN). If the fiber scope is not selected, the auxiliary light source drive circuit 33 activates the auxiliary light source at a pulse current and the control is returned (S51; N, S55, RETURN).

In the first embodiment mentioned above, the emission mode of the auxiliary light source 32 is manually selected by a user. In a second embodiment illustrated in FIG. 8, whether the light guide is mounted or the electronic endoscope is mounted is checked and the emission mode is automatically selected in accordance with the detection result. Whether or not he light guide is mounted is detected by the light guide detection sensor 41 provided in the vicinity of the light guide connector 21a. Whether or not the electronic endoscope is mounted is detected by the electronic connector detection sensor 42 provided in the vicinity of the electric connector 21. The sensors 41 and 42 can be each made of a contact sensor, such as a mechanical micro switch or a non-contacting sensor, such as a magnetic sensor or an optical sensor.

Figure 8:
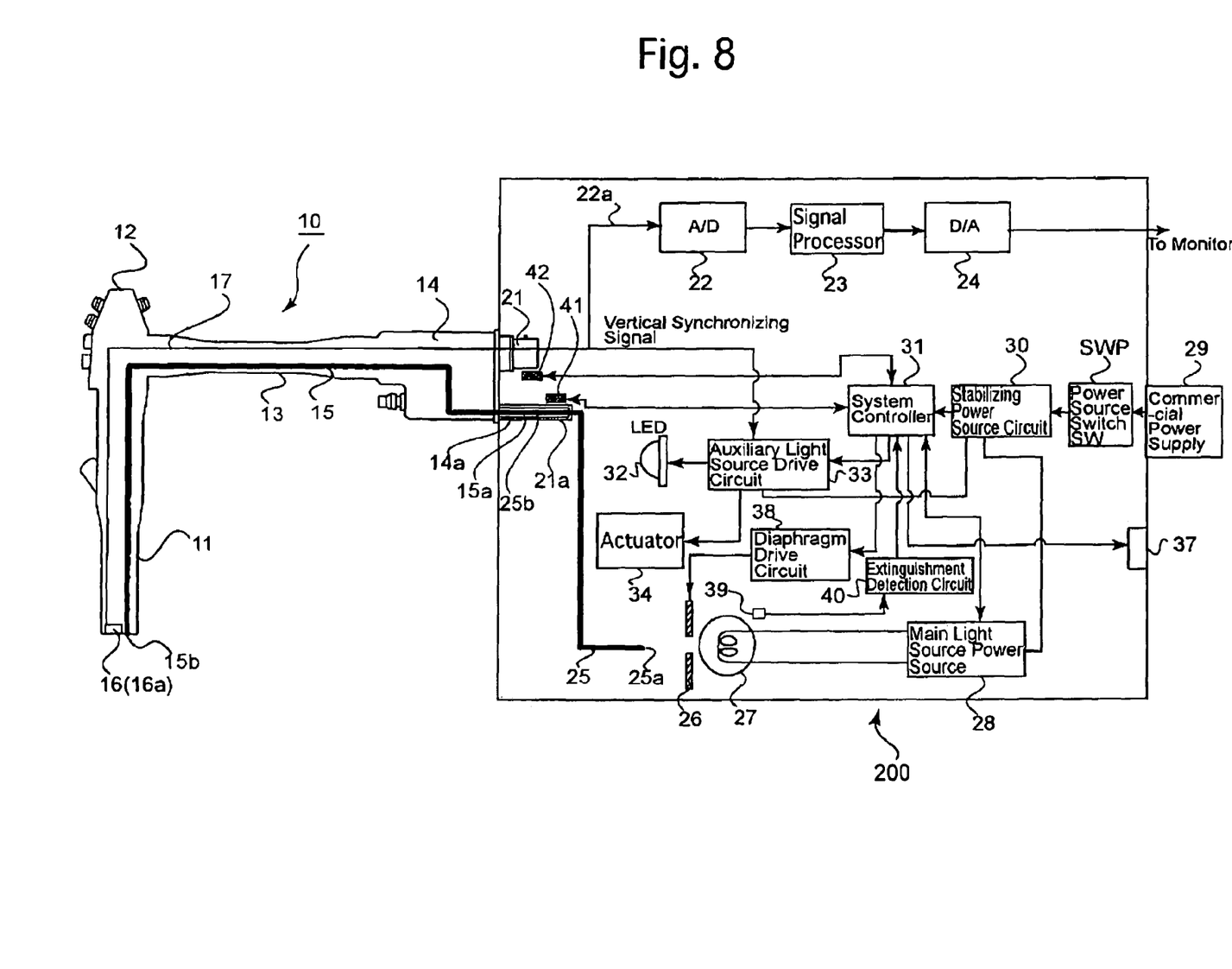
FIG. 8 is a block diagram of main components of an electronic scope system according to a second embodiment of the present invention.

When it is detected by the detection sensors 41, 42 that the electronic endoscope having the light guide and the electronic connector is mounted, the system controller 31 sets the pulse current emission mode. When it is detected that a scope (fiber scope) other than the electronic endoscope, but having the light guide is mounted, the system controller 31 sets the steady-state current emission mode. When it is detected that no light guide is mounted, no emission of light by the main light source 27 and the auxiliary light source 32 is permitted.

Figure 9:
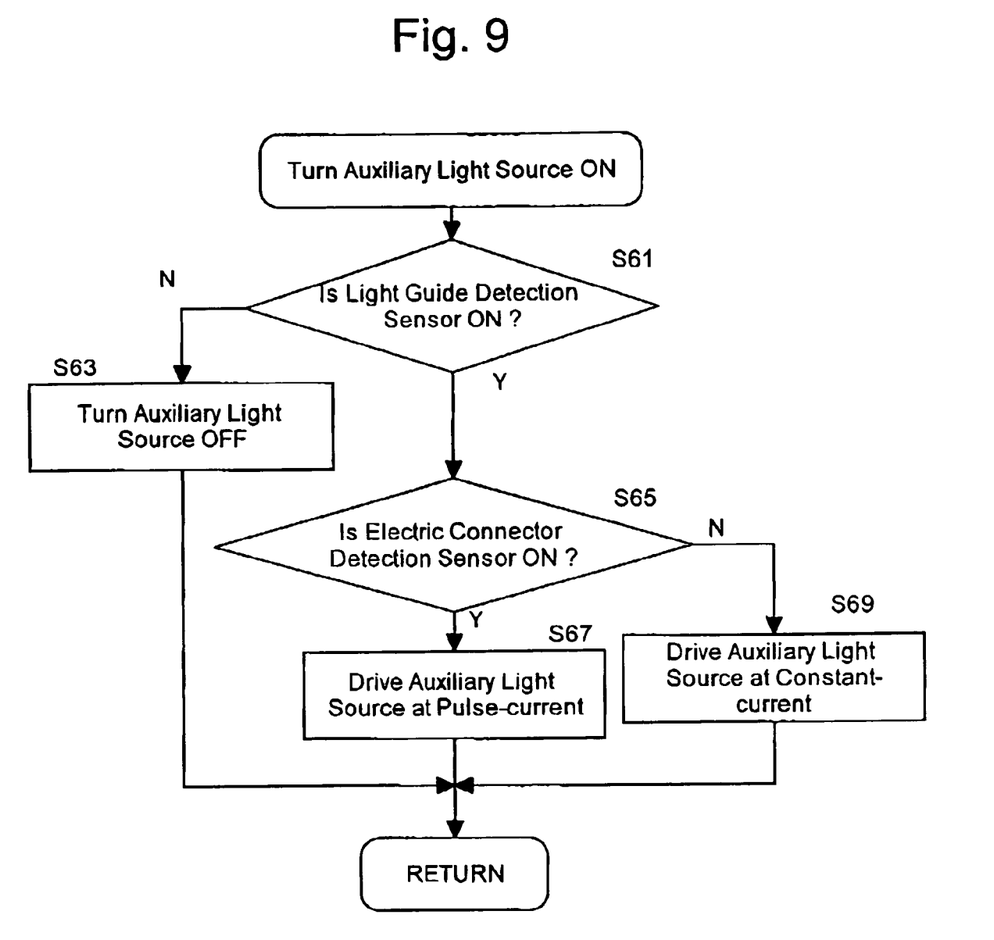
FIG. 9 is a flow chart of a light source activating operation in a second embodiment of the present invention.

The operation to turn the auxiliary light source in the second embodiment will be discussed below with reference to a flow chart shown in FIG. 9. The operation in this flow chart is performed as a sub-routine of S23 in FIG. 6.

In this flow chart, whether or not the light guide detection sensor 41 is ON (whether or not the light guide is connected) is checked (S61). If the light guide detection sensor is not turned ON, (no light guide is mounted), the auxiliary light source 32 is turned OFF and the control is returned (S61; N, S63, RETURN). If the light guide detection sensor 41 is ON (the light guide is mounted), whether or not the electric connector detection sensor 42 is ON (the electronic endoscope is mounted) is checked if the electric connector detection sensor 42 is ON (the electronic endoscope is mounted), the auxiliary light source drive circuit 33 is driven at the pulse-current emission mode to activate the auxiliary light source 32 at a pulse-current, and the control is returned (S61; Y, S65; Y, S67, RETURN). If the electric connector detection sensor 42 is not ON (the electronic scope is not mounted), the auxiliary light source drive circuit 33 is driven at the steady-state current emission mode to activate the auxiliary light source 32 at a constant current and the control is returned (S65; N, S69, RETURN).

In the second embodiment mentioned above, whether or not a scope having a light guide is mounted or whether or not an electronic endoscope is mounted are checked by the detection sensors 41, 42. The drive method of the auxiliary light source 32, i.e., the steady-state current emission mode or the pulse-current emission mode is automatically determined in accordance with the detection result. Therefore, it is not necessary for a user to determine the emission mode.

Figure 6:
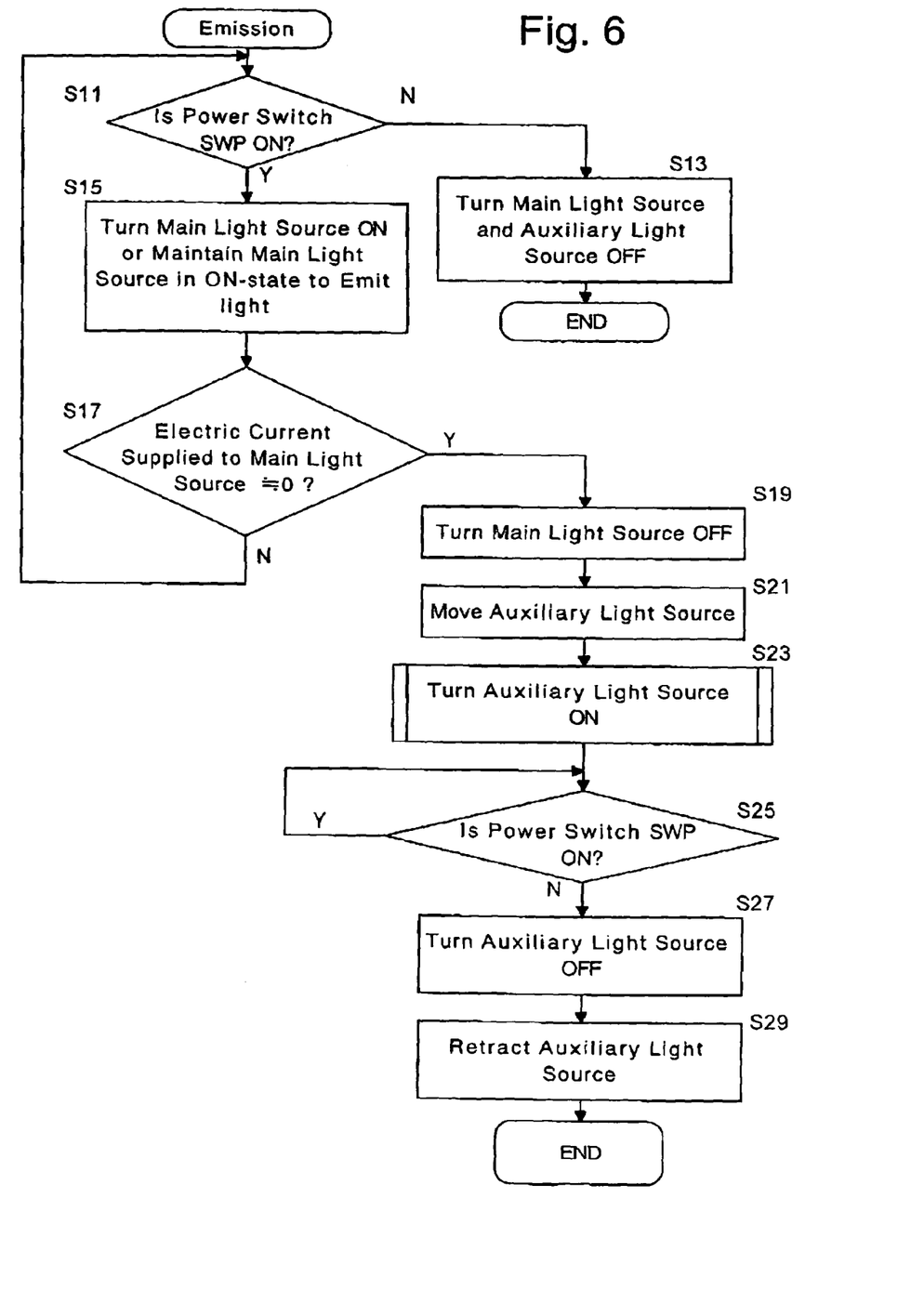
FIG. 6 is a flow chart of a light source activating operation in a first embodiment of the present invention.

In the second embodiment, it is preferable that a checking operation to check whether or not the light guide detection sensor 41 is ON is carried out before S11 (including a case when N on S17) and after the control is returned from the sub-routine of S23 to the main routine, for example, in the emission control operation in FIG. 6. In this alternative, if the light guide detection sensor 41 is OFF or is turned OFF, that is, if the light guide is not mounted or removed, both the main light source 27 and the auxiliary light source 32 are turned OFF.

As may be understood from the above discussion, according to the present invention, the main light source and the auxiliary light source are provided, wherein if the auxiliary light source is used to emit light, in place of the main light source, the continuous emission or the intermittent emission of light by the auxiliary light source can be selected. Accordingly, an appropriate illumination by the auxiliary light source can be obtained in accordance with circumstances.

What is claimed is:

1. A light source apparatus for an endoscope, comprising:
   a main light source;
   a light guide member whose incident end face is opposed to the main light source to guide light incident thereon to an emission end face thereof;
   an auxiliary light source that is activated to emit light when no light is emitted from the main light source, and that is supported to move between a stand-by position in which the auxiliary light source is located out of a main light path between the main light source and an incident end face of the light guide member and an operative position in which the auxiliary light source is located in the main light path and is opposed to the incident end face of the light guide member when the main light source is inoperative; and
   an auxiliary light source emission controller that drives the auxiliary light source at one of a continuous emission mode to emit light of a predetermined intensity and an intermittent emission mode to emit light of an intensity higher than the predetermined intensity,
   wherein the auxiliary light source comprises a light emitting diode (LED), and said auxiliary light source emission controller drives the light emitting diode at a constant current smaller than an absolute maximum rated value of a forward current of the light emitting diode when the continuous emission is performed, and drives the light emitting diode at a pulse current of which a crest value is higher than the absolute maximum rated value of the forward current when the intermittent emission is performed.

2. The light source apparatus of claim 1, wherein the light source apparatus is used with an endoscope processor to which one of an electronic endoscope and a fiber scope can be mounted, and wherein said auxiliary light source emission controller drives the auxiliary light source to emit light intermittently in synchronization with an image pickup operation of an image pickup device of the electronic endoscope when the electronic endoscope is connected to the endoscope processor and drives the auxiliary light source to emit light continuously when the fiber scope is connected to the endoscope processor.

3. The light source apparatus of claim 2, wherein said auxiliary light source emission controller drives the auxiliary light source to emit light intermittently in synchronization with a vertical synchronizing signal to drive the image pickup device.

4. The light source apparatus of claim 1, further comprising a selection switch that selects one of the intermittent emission of the auxiliary light source, at a pulse current, and the continuous emission of the auxiliary light source, through the auxiliary light source emission controller.

5. The light source apparatus of claim 1, further comprising a sensor that detects whether an electronic endoscope having the light guide member is mounted to an endoscope processor, wherein said auxiliary light source emission controller drives the auxiliary light source at a pulse current when the sensor detects that the electronic endoscope having the light guide member is mounted.

6. A light source apparatus for an endoscope, comprising:
   a main light source;
   a light guide member whose incident end face is opposed to the main light source to guide light incident thereon to an emission end face thereof;
   an auxiliary light source that is activated to emit light when no light is emitted from the main light source, and that is supported to move between a stand-by position in which the auxiliary light source is located out of a main light path between the main light source and an incident end face of the light guide member and an operative position in which the auxiliary light source is located in the main light path and is opposed to the incident end face of the light guide member when the main light source is inoperative; and
   an auxiliary light source emission controller that drives the auxiliary light source at one of a continuous emission mode to emit light of a predetermined intensity and an intermittent emission mode to emit light of an intensity higher than the predetermined intensity,
   wherein said auxiliary light source emission controller drives the auxiliary light source at a constant current smaller than an absolute maximum rated value of a forward current of the auxiliary light source when the continuous emission is performed, and drives the auxiliary light source at a pulse current of which a crest value is higher than the absolute maximum rated value of the forward current when the intermittent emission is performed.

7. The light source apparatus of claim 6, wherein the light source apparatus is used with an endoscope processor to which one of an electronic endoscope and a fiber scope can be mounted, and wherein said auxiliary light source emission controller drives the auxiliary light source to emit light intermittently in synchronization with an image pickup operation of an image pickup device of the electronic endoscope when the electronic endoscope is connected to the endoscope processor and drives the auxiliary light source to emit light continuously when the fiber scope is connected to the endoscope processor.

8. The light source apparatus of claim 7, wherein said auxiliary light source emission controller drives the auxiliary light source to emit light intermittently in synchronization with a vertical synchronizing signal to drive the image pickup device.

9. The light source apparatus of claim 6, further comprising a selection switch that selects one of the intermittent emission of the auxiliary light source, at a pulse current, and the continuous emission of the auxiliary light source, through the auxiliary light source emission controller.

10. The light source apparatus of claim 6, further comprising a sensor that detects whether an electronic endoscope having the light guide member is mounted to an endoscope processor, wherein said auxiliary light source emission controller drives the auxiliary light source at a pulse current when the sensor detects that the electronic endoscope having the light guide member is mounted.

* * * * *